United States Patent
Adams

(10) Patent No.: US 6,346,112 B2
(45) Date of Patent: *Feb. 12, 2002

(54) HEMOSTATIC CLIPS

(75) Inventor: Ronald Adams, Holliston, MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/730,845

(22) Filed: Dec. 7, 2000

Related U.S. Application Data

(63) Continuation of application No. 09/422,987, filed on Oct. 22, 1999, now Pat. No. 6,193,733, which is a continuation of application No. 08/879,931, filed on Jun. 20, 1997, now Pat. No. 6,001,110.

(51) Int. Cl.[7] ............................................. A61B 17/08
(52) U.S. Cl. ...................................................... 606/157
(58) Field of Search ................................. 606/153, 219, 606/151, 191, 192, 193, 194, 195, 222, 223, 76, 78, 157, 158; 604/95.05

(56) References Cited

U.S. PATENT DOCUMENTS

| 4,485,816 A | 12/1984 | Krumme | 606/219 |
| 4,505,767 A | 3/1985 | Quin | 148/402 |
| 4,586,502 A | 5/1986 | Bedi et al. | 128/334 |
| 4,665,906 A | 5/1987 | Jervis | 128/92 |
| 4,969,300 A | 11/1990 | Anderson | 128/334 |
| 5,002,563 A | * 3/1991 | Pyka et al. | 606/222 |
| 5,067,957 A | 11/1991 | Jervis | |
| 5,190,546 A | 3/1993 | Jervis | |
| 5,258,008 A | 11/1993 | Wilk | 606/219 |
| 5,597,378 A | 1/1997 | Jervis | |
| 5,632,746 A | 5/1997 | Middleman et al. | 606/78 |
| 5,695,504 A | 12/1997 | Gifford, III et al. | 606/153 |

FOREIGN PATENT DOCUMENTS

| EP | 0 826 340 | 3/1998 |
| WO | WO96/16603 | 6/1996 |
| WO | WO97/18762 | 5/1997 |

* cited by examiner

Primary Examiner—Henry J. Recla
Assistant Examiner—Vy Q. Bui
(74) Attorney, Agent, or Firm—Kenyon & Kenyon

(57) ABSTRACT

Clips having pseudoelastic properties at body temperature are used to cause hemostatis of blood vessels located along the gastrointestinal tract. Methods for causing the hemostasis of blood vessels and ulcer beds using the clips of the present invention are also disclosed.

6 Claims, 12 Drawing Sheets

HEMOSTATIC CLIPS

This application is a continuation of application Ser. No. 09/422,987, filed Oct. 22, 1999, now U.S. Pat. No. 6,193,733 which is a continuation of application Ser. No. 08/879,931, filed Jun. 20, 1997 now, U.S. Pat. No. 6,001,110.

FIELD OF THE INVENTION

The present invention relates to hemostatic clips, and more specifically, to pseudoelastic nitinol clips which are used to cause hemostasis of blood vessels located along the gastrointestinal tract.

BACKGROUND OF THE INVENTION

Gastrointestinal bleeding is a somewhat common and serious condition that can be fatal if left untreated. This problem has prompted the development of a number of endoscopic therapeutic approaches to achieve hemostasis, such as the injection of sclerosing agents and contact thermo-coagulation techniques. Although such approaches can be effective, bleeding often continues for many patients and corrective surgery therefore becomes necessary. Because surgery is an invasive technique that can be associated with many undesirable side effects, there exists the need for highly effective, less invasive procedures.

Mechanical hemostatic devices have been used in various parts of the body, including gastrointestinal applications. Such devices are typically in the form of clamps, clips, staples, sutures, etc. which are able to apply sufficient constrictive forces to blood vessels so as to limit or interrupt blood flow. One of the problems associated with conventional hemostatic devices, however, is that they can only be delivered using rigid-shafted instruments via incision or trocar cannula. Moreover, none of the conventional endoscopic hemostatic devices are strong enough to cause permanent hemostasis.

In order to avoid the problems associated with conventional hemostatic devices, the use of shape memory alloys has been proposed. For example, U.S. Pat. No. 4,485,816, hereby incorporated by reference, discloses the use of a shape memory surgical staple for use in holding the edges of a wound together while it heals. Similarly, U.S. Pat. No. 5,002,563, hereby incorporated by reference, discloses the use of shape memory sutures.

Shape memory alloys (SMA's) have the ability to "remember" specific shapes which corresponds to particular metallurgical phases. If deformed, SMA's can be heated or cooled to invoke a phase transformation, which in turn, causes a transformation in shape. Shape memory alloys are, characterized by a transition temperature or transition temperature range, above which the predominant metallurgical phase is termed austenite and below which the predominant phase is termed martensite. The transformation temperatures of SMA's are commonly discussed with reference to $M_s$ and $M_f$, the martensitic start and finish temperatures, respectively, and $A_s$ and $A_f$, the austenitic start and finish temperatures, respectively. The transformation between these phases is reversible such that when alloys are deformed into some first configuration while in the austenitic state, cooled into a martensitic state, deformed into a second configuration, and then re-heated to the austenitic state, the alloy will revert back to the first configuration by virtue of the martensite-to-austenite phase transformation.

PCT Publication No. WO 96/16603, hereby incorporated by reference, specifically discloses the use of shape memory materials to address the problem of gastrointestinal bleeding. In this reference, a hemostatic staple is employed to affect hemostasis of an actively bleeding peptic ulcer. The staple makes use of the thermally-induced martensite-to-austenite transformation in shape memory nickel-titanium alloys ("nitinol"), thus requiring the application or removal of heat to the staple for deployment. One of the problems with this and similar SMA devices is that the change in temperature necessary to induce the required shape change can be procedurally difficult, and more importantly, can put the nearby tissue and surgical instrumentation at risk. In addition, it can be difficult to manufacture SMA's with the precise transformation temperatures necessary for surgical applications. It is therefore necessary to carefully monitor the temperature of such devices during shipping and storage so as to avoid phase transformations during this time. Moreover, the thermally-induced phase change may not produce forces adequate to hemostatically close vessels or compress tissue.

The use of nitinol alloys having the ability to form stress-induced martensite as opposed to thermally-induced martensite has been used in medical devices so as to avoid the potential problems of SMA devices. In such alloys, the reversible transformation between martensite and austenite occurs by the application and removal of stress rather than heat. Such alloys are characterized by an $M_d$ temperature, which is greater than $A_s$ and represents the maximum temperature at which stress-induced martensite can form. By deforming these alloys at a temperature. between $A_s$ and $M_d$, the alloy transforms from its austenitic phase to a stress-induced martensitic phase. Upon release of the stress within this temperature range, the alloy reverts back to its austenitic phase and unstressed configuration. The property of nitinol which allows it to be deformed in its austenitic state so to cause a transformation to stress-induced martensite that is transformed back to austenite by the release of stress is often termed "pseudoelasticity." Strains of 8% or more are obtained in pseudoelastic nitinol, thus making this material useful for a wide range of applications where a large amount of recoverable deformation is required.

U.S. Pat. No. 4,665,906, incorporated herein by reference, describes some medical devices which make use of pseudoelastic nitinol. In such devices, austenitic nitinol is deformed to form stress-induced martensite and held in its deformed configuration and martensitic state by a restraining member. In this condition, the device is introduced into the body, where it is removed from the restraining member to return to its austenitic state and configuration.

SUMMARY OF THE INVENTION

The present invention is directed to hemostatic clips which exhibit pseudoelastic properties at body temperature. The clips of the present invention are able to compress tissue to cause the hemostasis of bleeding blood vessels, particularly gastrointestinal bleeders. In one embodiment of the present invention, the clips have a "U"-shaped configuration when in an undeformed state. In a second embodiment of the present invention, the clips have a circular-shaped configuration when in an undeformed state. The present invention includes methods and systems for causing the hemostasis of blood vessels and ulcer beds located along the gastrointestinal tract using hemostatic clips.

One advantage of the present invention is that it provides a reliable, definitive treatment for the problem of gastrointestinal bleeding.

Another advantage of the present invention is that it can be delivered via natural body orifices for the control of gastrointestinal bleeding.

Another advantage of the present invention is that it provides hemostatic clips which are deployed without the application or removal of heat.

Yet another advantage of the present invention is that it provides hemostatic clips with sufficient strength to produce permanent hemostasis when deployed.

Another advantage of the present invention is that it provides hemostatic clips which are particularly designed for application to gastrointestinal bleeders.

DETAILED DESCRIPTION

The present invention is designed to address the problems encountered in conventional methods used to ligate blood vessels. More particularly, the present invention is adapted to restrict blood flow which results in gastrointestinal bleeding.

The present invention includes hemostatic clips which make use of pseudoelastic properties found in materials such as nitinol. Using these properties, the clips of the present invention are shaped into a first configuration that is useful for ligating blood vessels, deformed to a second configuration to facilitate placement to a desired location within the body, and released from its deformed configuration to allow a spontaneous reversion towards the first configuration.

The pseudoelastic material used to make the hemostatic clips of the present invention is characterized by an $A_s$ temperature less than body temperature and an $M_d$ temperature greater than body temperature. A clip in accordance with the present invention is thus provided with a first configuration in its austenitic state, which is deformed to a second configuration to facilitate the placement of the clip around or adjacent to a bleeding blood vessel. The deformation of the clip from its first configuration to its second configuration results in the formation of stress-induced martensite. The clip is held in its second configuration until positioned to a target location along the gastrointestinal tract. When released from this second configuration, the clip is urged toward its austenitic state and corresponding first configuration because $A_s$ is less than body temperature and austenite is therefore the stable metallurgical phase. In this way, the clip applies sufficient constrictive forces to the bleeding blood vessel to cause hemostasis thereof.

Figure 1A:
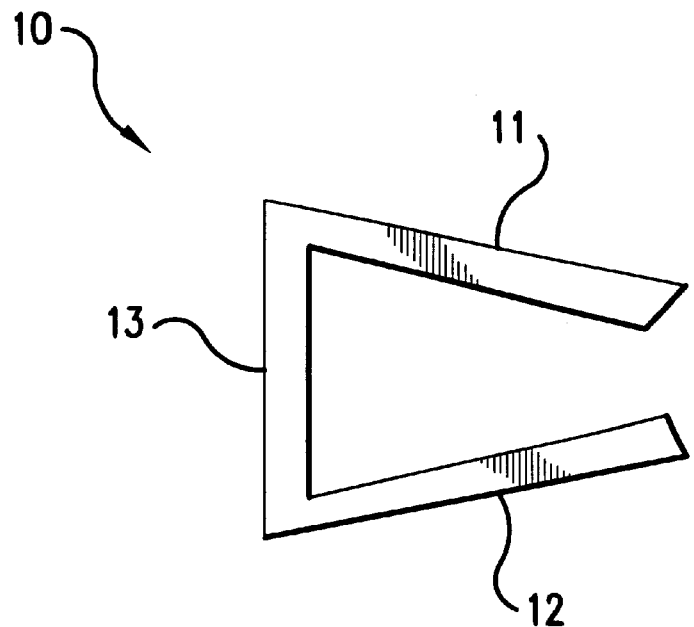
FIGS. 1A and 1B are plan views of a U-shaped hemostatic clip in a first and second configuration, respectively, in accordance with the present invention.

The hemostatic clips of the present invention are of any suitable configuration. In a first embodiment of the present invention as shown in FIG. 1, however, hemostatic clip 10 is in the form of a U-shaped wire having first 11 and second 12 prongs, and rear member 13. The diameter or width of rear member is less than that of either of the first 11 or second 12 prongs. The first configuration of clip 10 as shown in FIG. 1A represents the shape of clip 10 when in its substantially austenitic state. In this configuration, the distance between said first 11 and second 12 prongs is about 5–10 millimeters, preferably about 7 millimeters. This dimensional range is specifically designed to address the problem of gastrointestinal bleeders. The cross-section of clip 10 is preferably circular, although other cross-sectional shapes such as rectangular can be used.

Figure 1B:
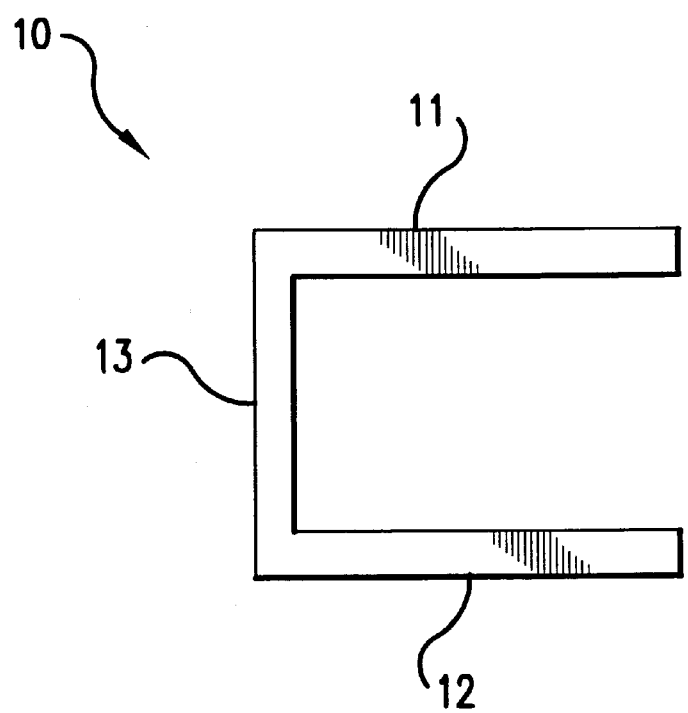

To facilitate placement around or near a blood vessel, prongs 11 and 12 are urged in an outward direction to achieve a second configuration as shown in FIG. 1B. The distance between prongs 11 and 12 in this second configuration can be up to 15 millimeters or more. When deformed into the shape shown in FIG. 1B from the shape shown in FIG. 1A, U-shaped clip 10 undergoes at least a partial stress-induced transformation from austenite to martensite.

Figure 2:
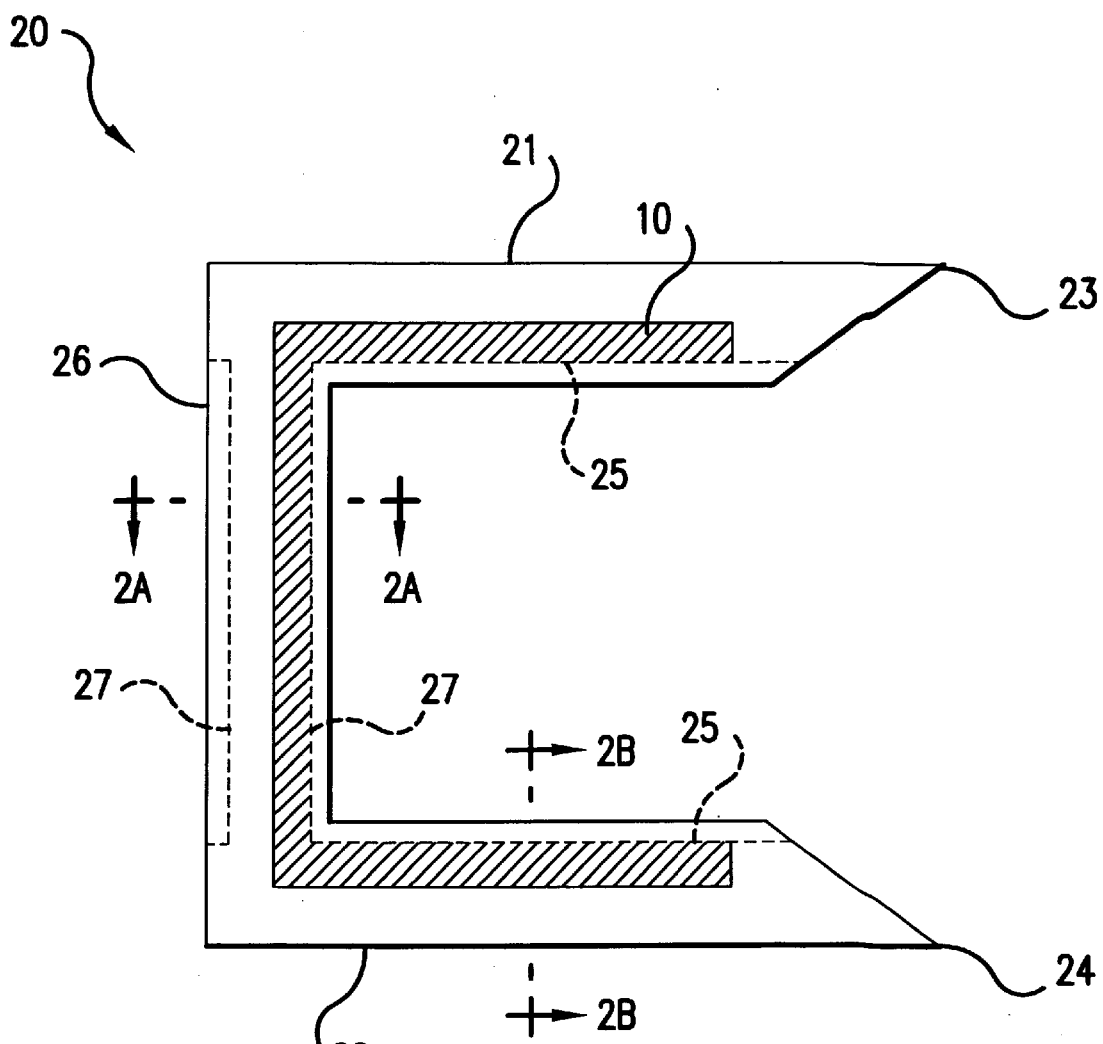
FIG. 2 includes plan and cross-sectional views of a hypotube of the present invention.
Figure 2A:
Figure 2B:
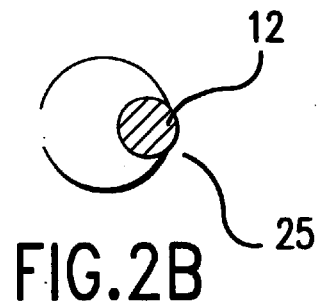

A device such as hypotube 20, as shown in FIG. 2, is used to hold U-shaped clip 10 in its second configuration while it is delivered to a target location along the gastrointestinal tract. Hypotube 20 is made of any suitable material, such as stainless steel.

Hypotube 20 includes first 21 and second 22 prongs having pointed ends 23 and 24, respectively. Along the length of the inner sides of first 21 and second 22 prongs are longitudinal slots 25. Along the length of both sides of rear member 26 are transverse slots 27. The width of slots 26 and 27 are wider than the width of rear member 13 of U-shaped clip 10, yet more narrow than first 11 and second 12 prongs of U-shaped clip 10. Such a configuration allows hypotube 20 to hold U-shaped clip 10 in its second configuration, while permitting the passage of U-shaped clip 10 through hypotube 20.

Figure 3:
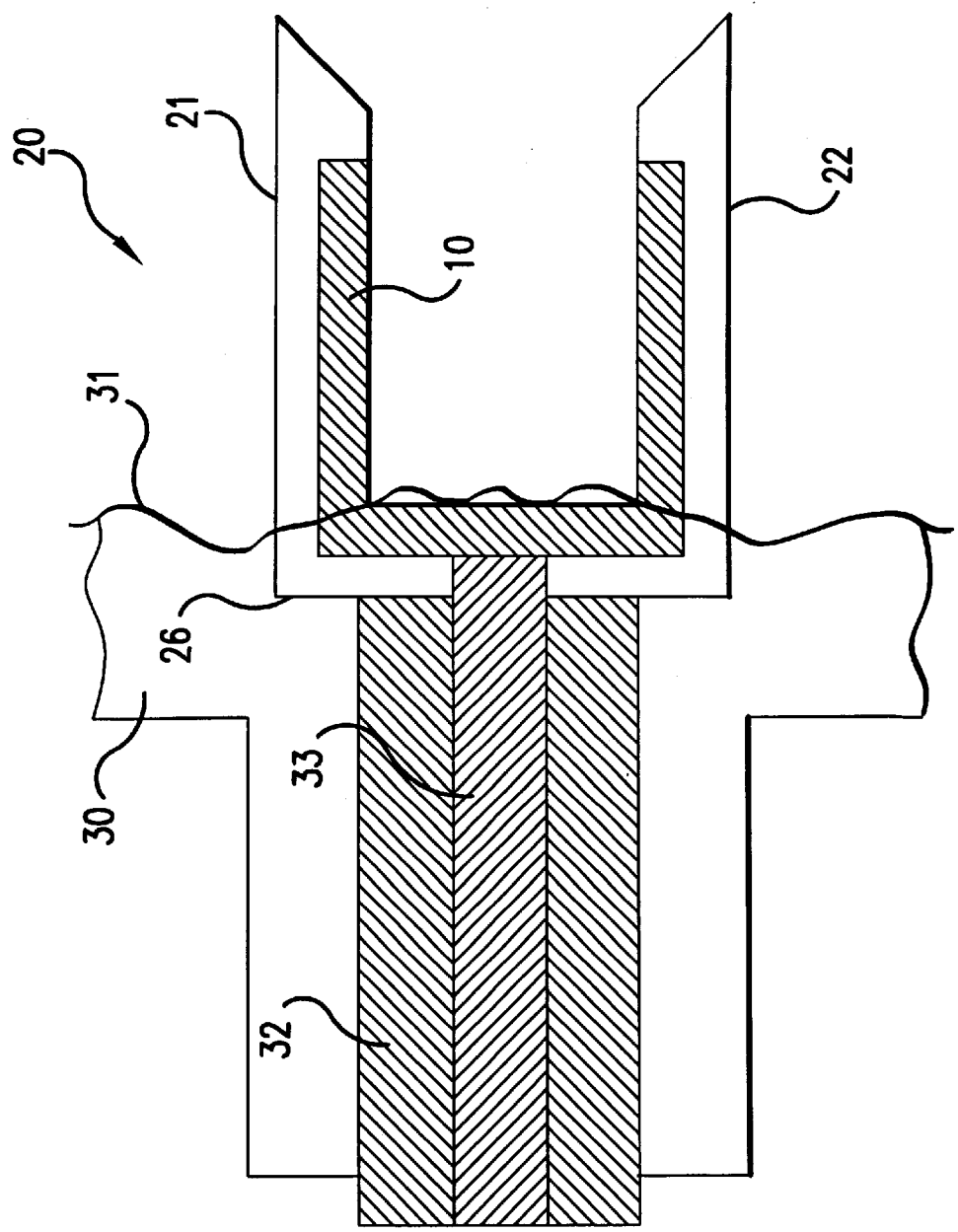
FIGS. 3–5 illustrate a method of deploying the hemostatic U-shaped clips of the present invention.

After placing clip 10 in hypotube 20, it is inserted as part of a delivery device 30 into the gastrointestinal tract, preferably via a natural body orifice. Upon reaching a target location, the pointed ends 23 and 24 of hypotube 20 are used to penetrate the gastrointestinal wall 31 by advancing a first pusher bar 32 which is attached to hypotube 20, as shown in FIG. 3. Also shown in FIG. 3 is second pusher bar 33, which rests against, but is not attached to, clip 10. Second pusher bar 33 is inserted through transverse slots 27 of hypotube 20 to contact clip 10. The length of prongs 21 and 22 are sufficient to ensure that the blood vessel to be treated is positioned between the prongs 11 and 12 of clip 10, or is within about one centimeter of the ends of prongs 11 and 12 of clip 10. The rear member 26 of hypotube 20 remains outside of the gastrointestinal wall.

Figure 4:
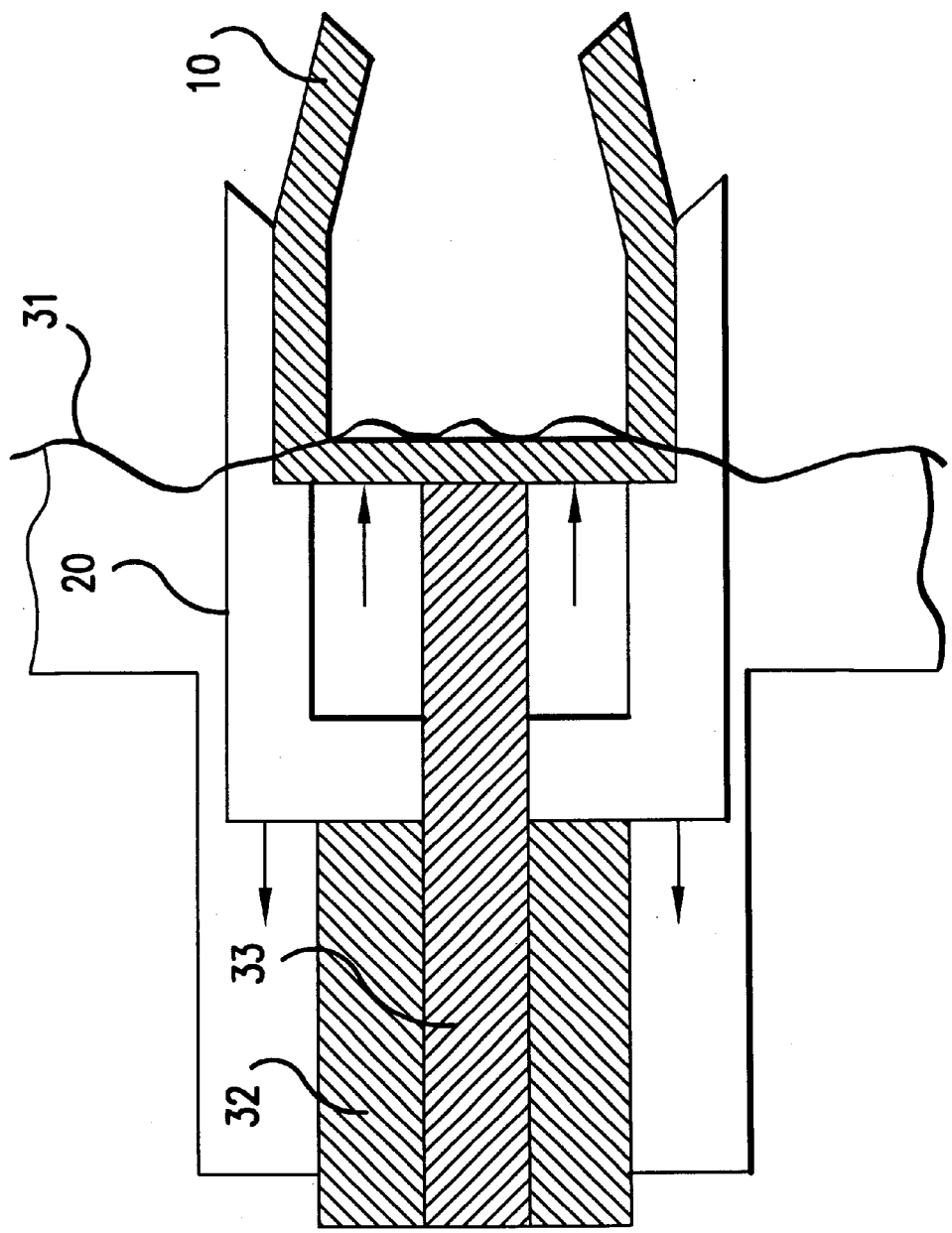
Figure 5:
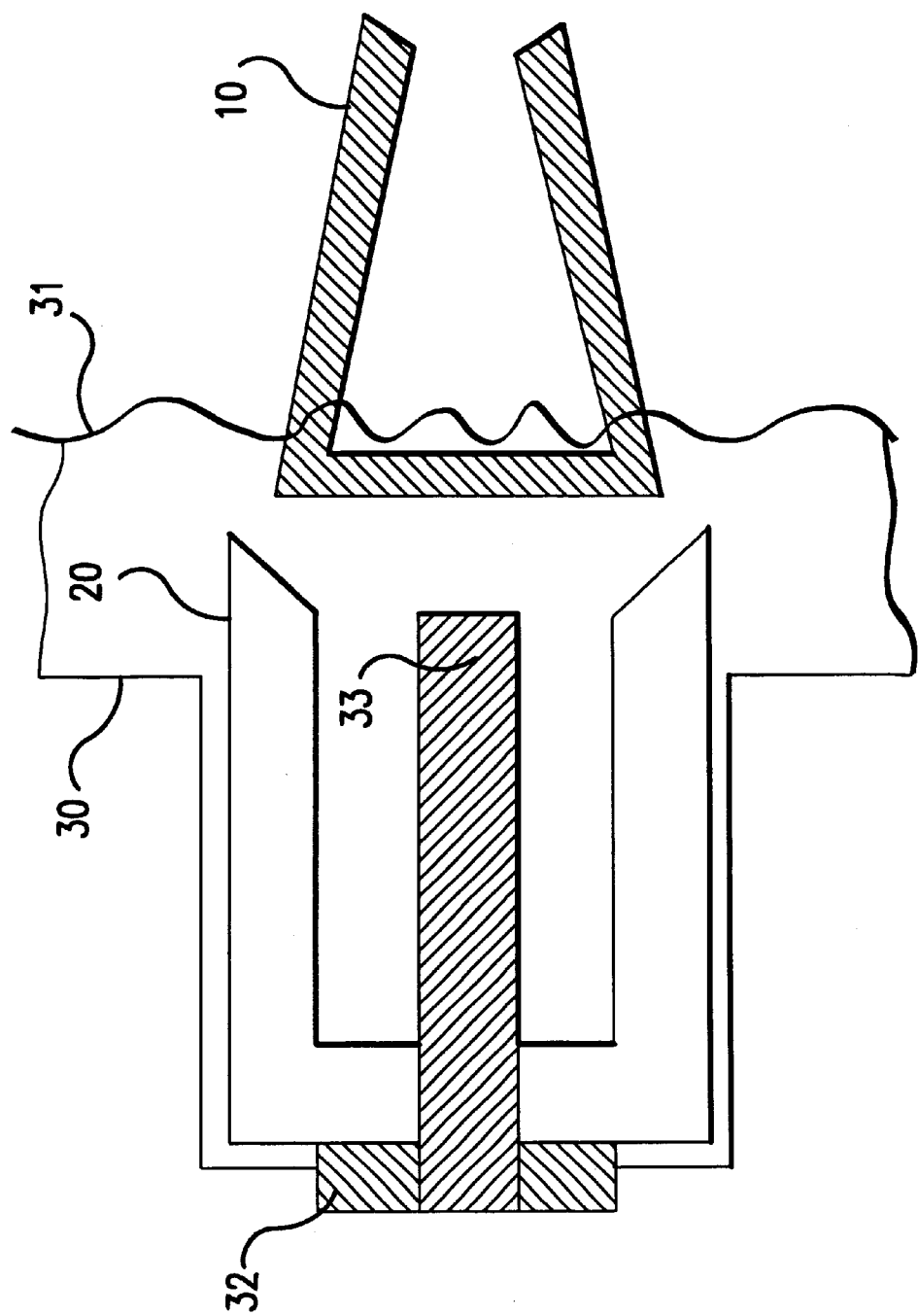

To deploy clip 10, hypotube 20 is withdrawn from the gastrointestinal wall 31 by retracting first pusher bar 32, as shown in FIG. 4. During the withdrawal of hypotube 20, second pusher bar 33 remains extended so to keep clip 10 at the target location. As clip 10 is released from hypotube 20, it is urged towards its austenitic configuration as shown in FIG. 4. When hypotube 20 is completely withdrawn from the gastrointestinal wall 31, the contact between second pusher bar 33 and clip 10 is broken as shown in FIG. 5.

The clips of the present invention are delivered by any suitable instrumentation, as is known in the art. For delivery of the clips via natural body orifices, which is the preferred method of delivery, it is usually necessary to deliver the clips with the aid of steerable endoscope to allow the physician installing the clips to visually examine the target location. "Endoscope" is intended to include similar instrumentation such as a gastroscope or duodenoscope.

Figure 6:
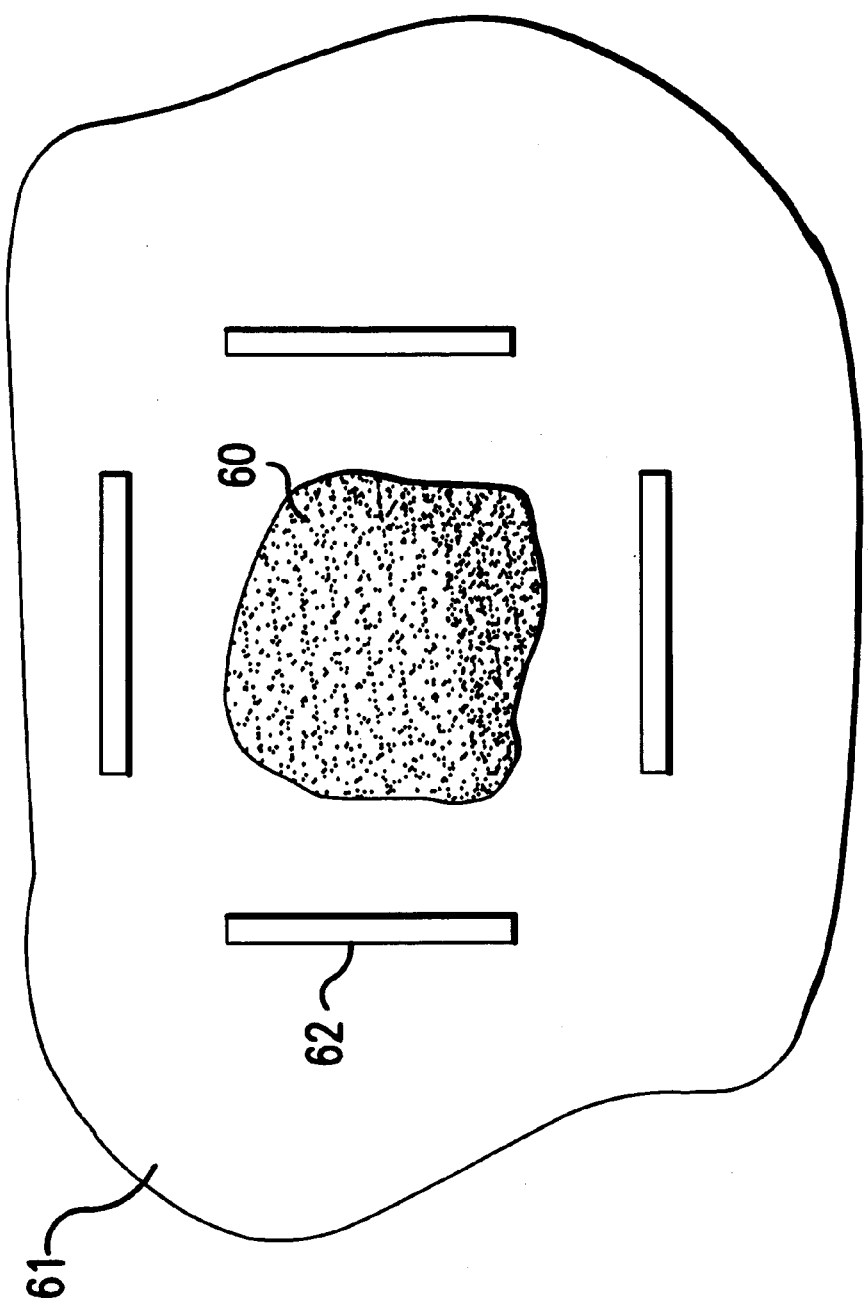
FIG. 6 is a plan view showing an ulcer bed surrounded by hemostatic clips, in accordance with the present invention.

In addition to causing the hemostasis of individual blood vessels, the present invention contemplates the use of hemostatic clips to cause the hemostasis of bleeding ulcer beds. In order to achieve the hemostasis of an ulcer bed, it is desirable to substantially surround the ulcer bed 60 with hemostatic clips 62, as shown in FIG. 6. This is preferably achieved with two pairs of hemostatic clips 62, each pair being substantially parallel to each other yet orthogonal to the other pair. The hemostatic clips 62 are deployed into the gastrointestinal wall 61 in the configuration shown in FIG. 6 so to reduce the flow of blood to ulcer bed 60. Each of the clips 62 should be within about 5 mm, preferably about 2 mm, and most preferably about 1 mm from the edge of ulcer bed 60.

Figure 7A:
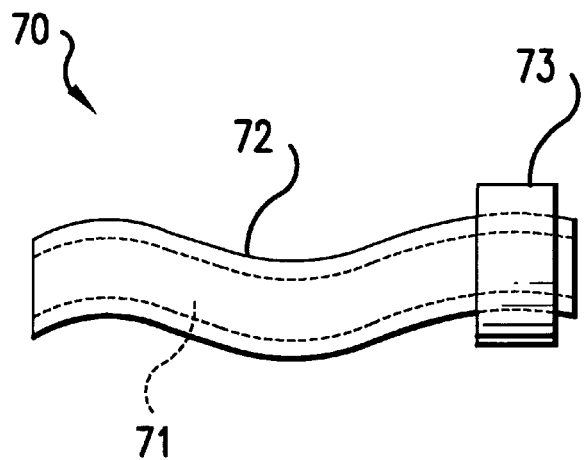
FIGS. 7A and 7B are plan and end views, respectively, of a delivery device used to deploy the U-shaped hemostatic clips of the present invention.
Figure 7B:
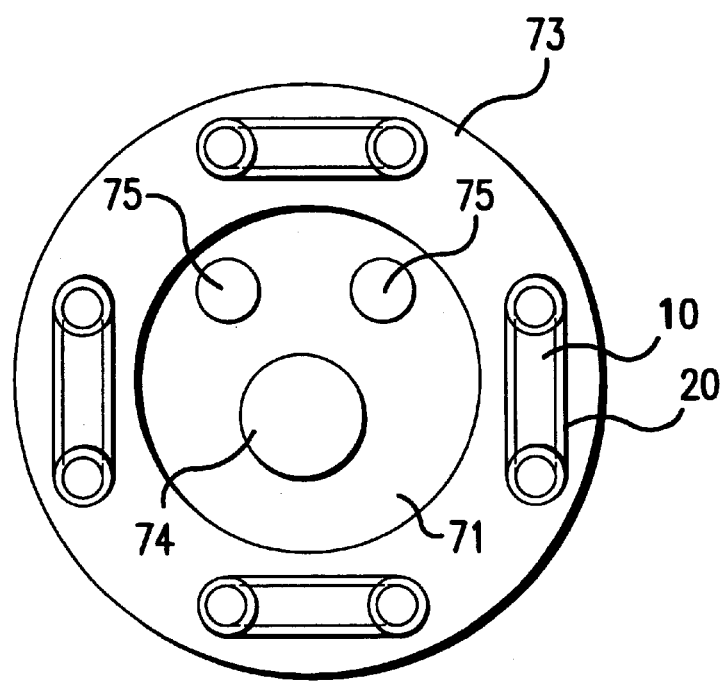
Figure 7C:
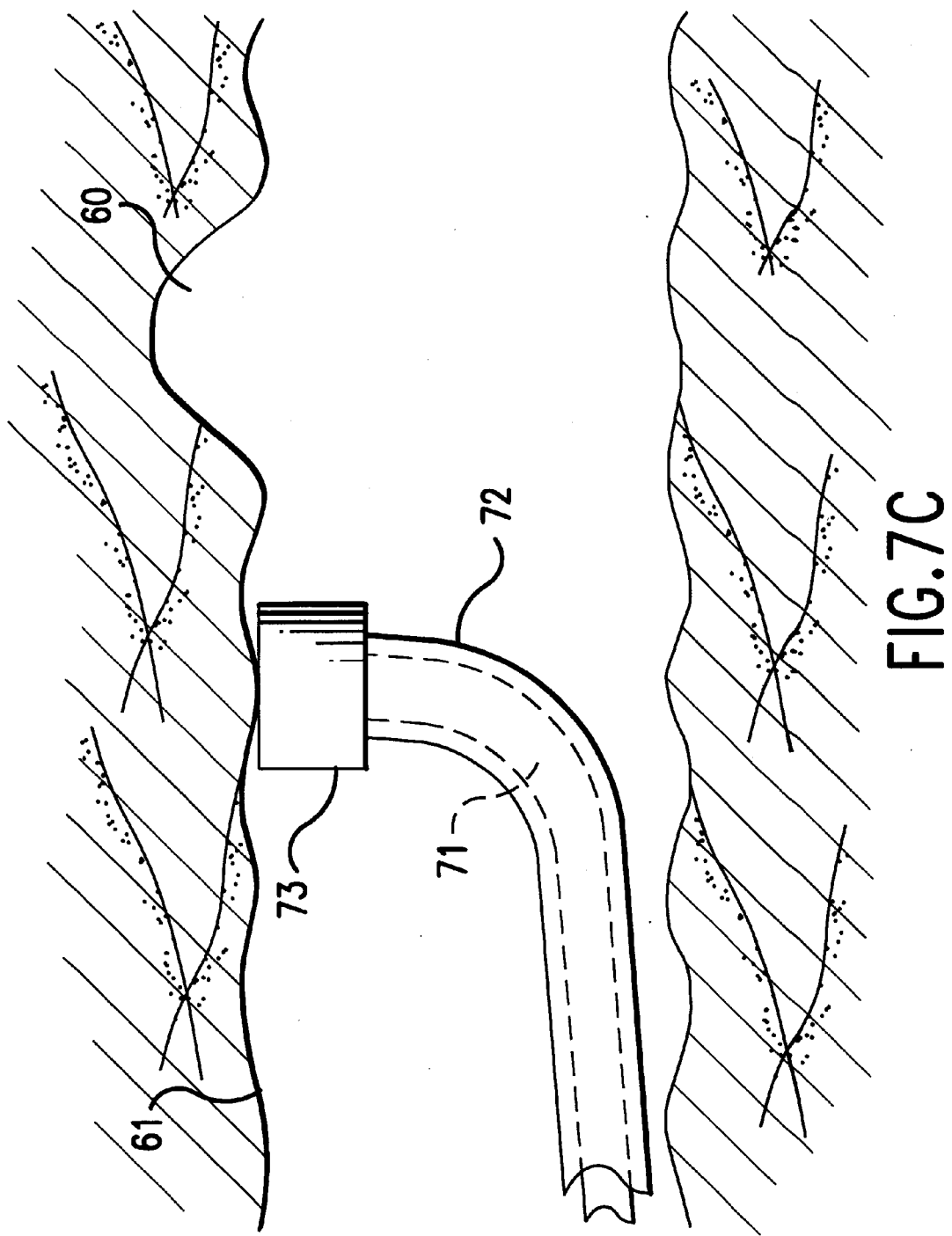
FIG. 7C is a plan view of a delivery device deploying the hemostatic clips of the present invention adjacent an ulcer bed.

In order to achieve the configuration of clips shown in FIG. 6, it is necessary to manipulate the clip delivery device to properly orient the clips prior to insertion. This can be done with steerable endoscopes, as are known in the art, provided that the clips are deployed in regions of the gastrointestinal tract that are wide enough to permit such manipulation (e.g., the stomach or lower bowel). In narrow regions of the gastrointestinal tract (e.g., the duodenum), however, it may be necessary to use a delivery device in which the clips are pre-loaded in the proper orientation. An example of such a device is shown in FIGS. 7A–7C. As shown in FIG. 7A, delivery device 70 comprises an endoscope 71 having a sheath 72 ending in a collar 73 that houses the hemostatic clips. As shown in FIG. 7B, the clips 10 are oriented for the deployment configuration as shown in FIG. 6. As is known in the art, endoscope 71 includes optics 74 and at least one light 75. Sheath 72 is used to house any wires, instrumentation, etc. necessary to deploy clips 10 from collar 73. In addition, sheath 72 is optionally slidable about endoscope 71 to permit rotation of collar 73 and the corresponding axial positioning of clips 10. Although U-shaped clips 10 are shown in FIG. 7B, collar 73 is easily adapted for the deployment of hemostatic clips having a circular or other configuration. To deploy clips 10, endoscope 71 is oriented so that the surface of collar 73 is adjacent the gastrointestinal wall 61 as shown in FIG. 7C. Clips 10 are thereafter inserted into the gastrointestinal wall 61 so as to substantially surround ulcer bed 60 in an arrangement as shown in FIG. 6.

Figure 8A:
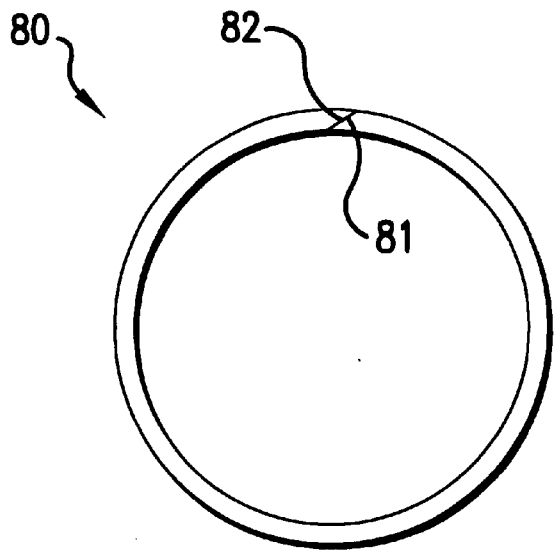
FIGS. 8A and 8B are plan views of circular hemostatic clips of the present invention.
Figure 8B:
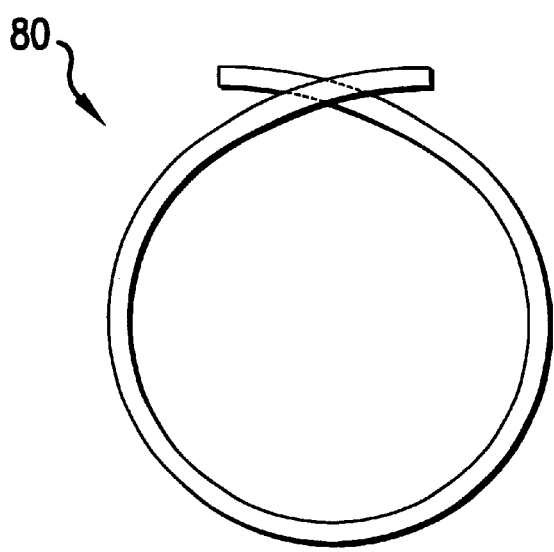

In another embodiment of the present invention, the nitinol hemostatic clip of the present invention is in a substantially circular configuration when it is in a substantially austenitic state, as shown in FIG. 8. Circular clip 80 has a diameter of about 5–10 millimeters, and preferably about 7 millimeters when in its austenitic configuration. This dimensional range is specifically designed to address the problem of gastrointestinal bleeders. Circular clip 80 can have interlocking or adjoining ends 81, 82, as shown in FIG. 8A, or overlapping ends as shown in FIG. 8B.

To facilitate placement around or near a blood vessel, the ends of circular clip 80 are urged away from each other so that clip 80 achieves some second configuration that permits clip deployment. This second configuration typically has a straightened or arc shape. When deformed into this second configuration, circular clip 80 undergoes at least a partial stress-induced transformation from austenite to martensite.

Figure 9:
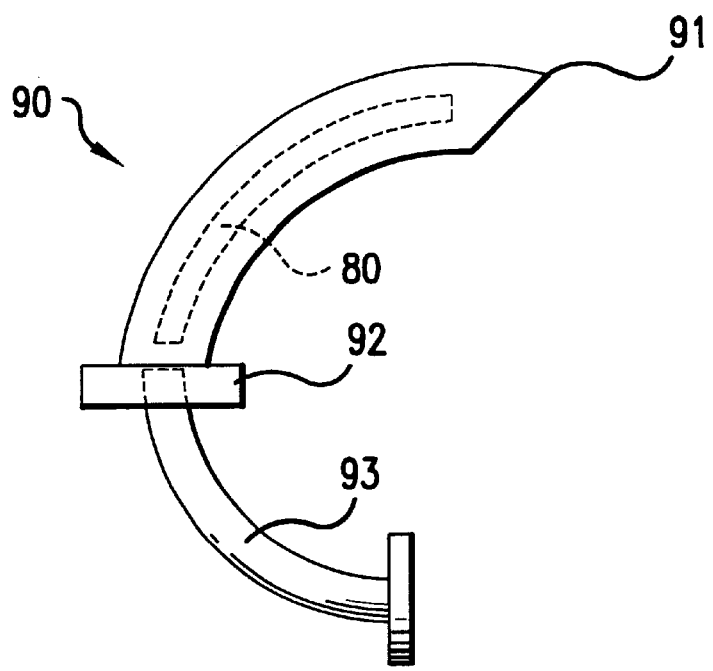
FIG. 9 is a plan view of a hypodermic needle of the present invention.

A device such as hypodermic needle 90, as shown in FIG. 9, is used to hold circular clip 80 in its second configuration while it is delivered to a target location along the gastrointestinal tract. Hypodermic needle has an arc configuration and includes pointed end 91, base 92 and pusher bar 93. Hypodermic needle 90 is made of any suitable material, although stainless steel is preferred.

Figure 10:
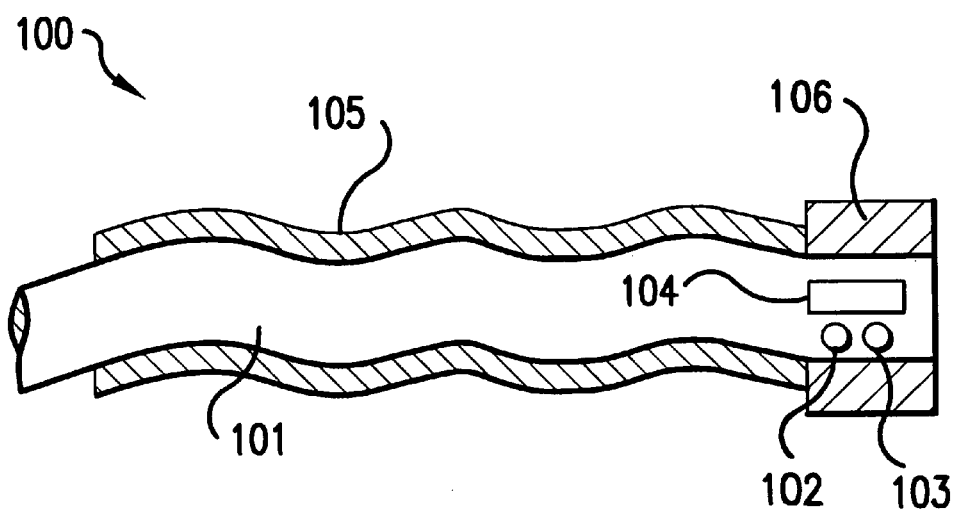
FIG. 10 is a plan view of a delivery device used to deploy the circular hemostatic clips of the present invention.

Circular clip 80 is delivered to a target location along the gastrointestinal tract by any suitable instrumentation, as is known in the art. Circular clip 80 is preferably delivered with the delivery device shown in FIG. 10. Delivery device 100 includes a duodenoscope 101 having side-mounted optics 102, at least one side-mounted light 103 and grasper 104. Sheath 105, ending in collar 106, covers only part of the circumference of duodenoscope 101 so as not to cover the optics 102, light 103 or grasper 104.

Figure 11A:
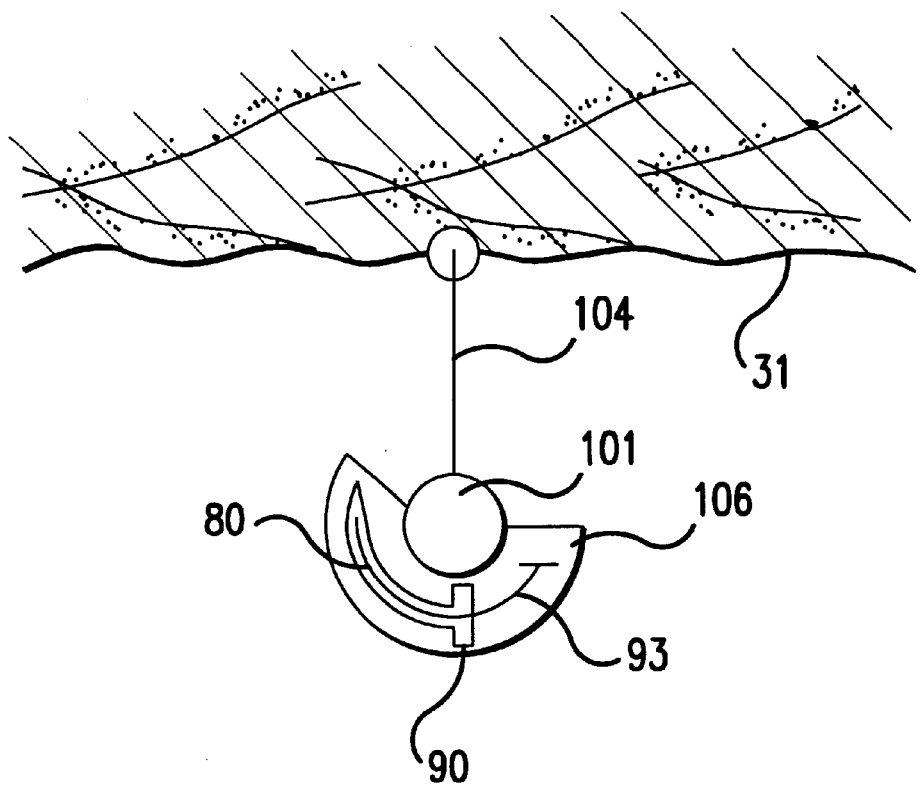
FIGS. 11A–11D illustrate a method of deploying the hemostatic circular clips of the present invention.
Figure 11B:
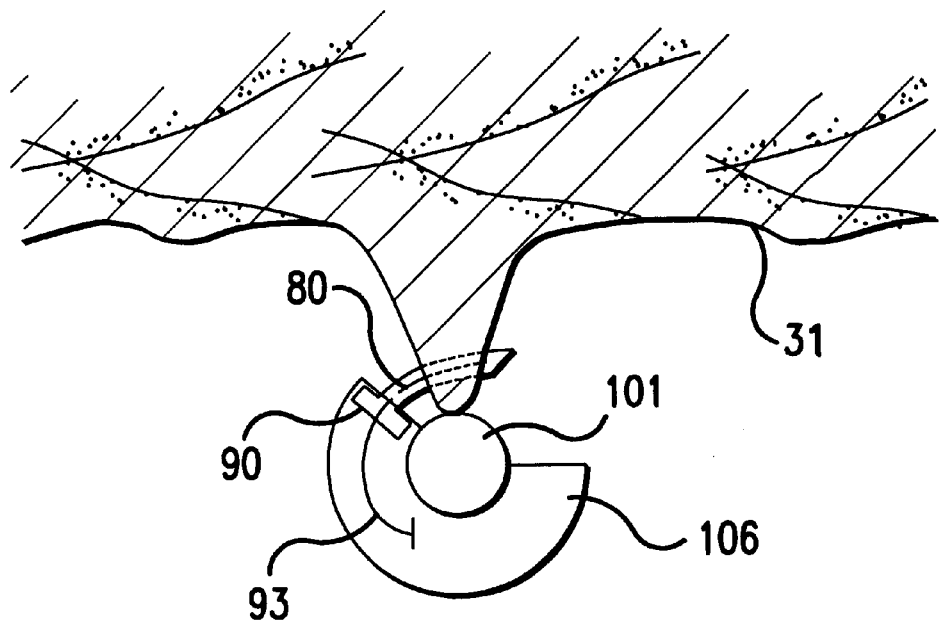
Figure 11C:
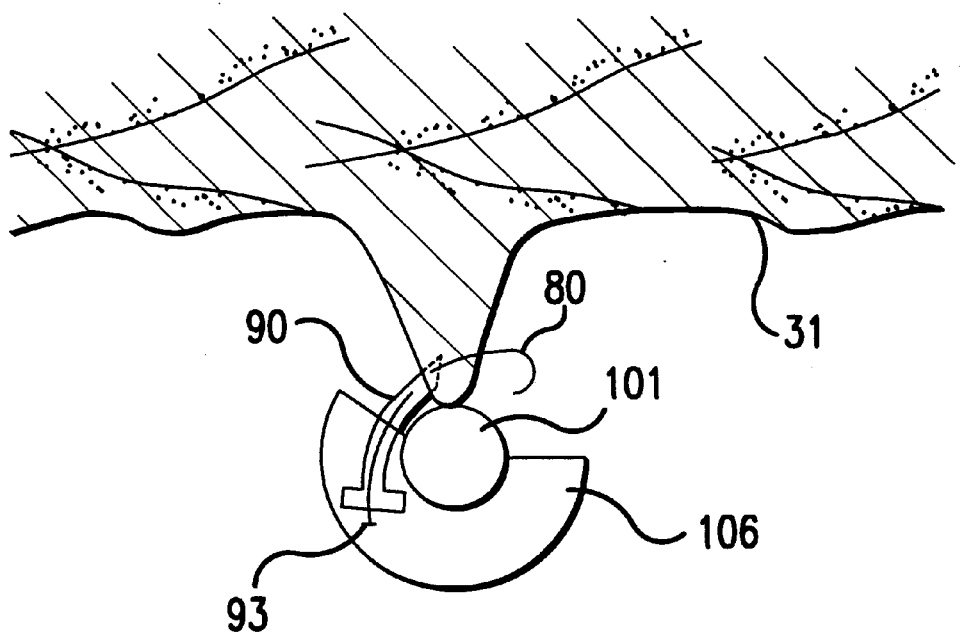
Figure 11D:
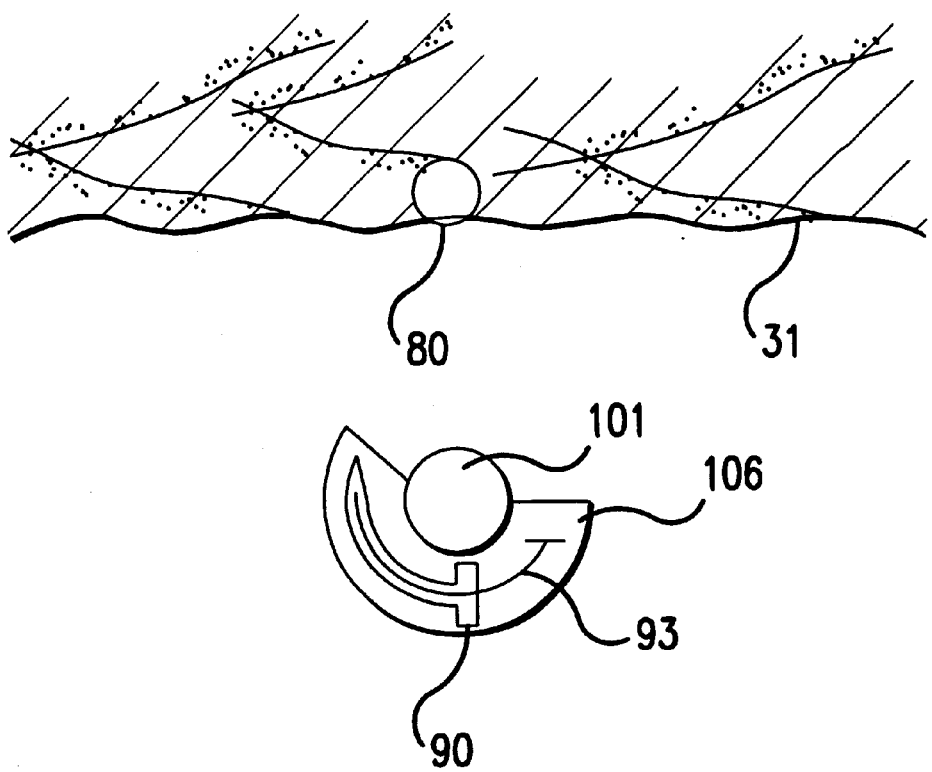

Delivery device 100 is used to deliver circular clip 80 by the method shown in FIGS. 11A–11D. As shown in FIG. 11A, the delivery device 100 is delivered to a target location along the gastrointestinal tract. Grasper 104 is used to grasp the gastrointestinal wall 31 and pull it towards the duodenoscope 101. As shown in FIG. 11B, hypodermic needle 90 penetrates the pulled portion of the gastrointestinal wall and is advanced to a desired location while housing circular clip 80 and pusher bar 93. Circular clip 80 is released by retracting hypodermic needle 90 from the pulled gastrointestinal wall while holding the clip 80 with pusher bar 93. After hypodermic needle 90 is fully retracted from the pulled gastrointestinal wall, pusher bar 93 is likewise retracted into collar 106. The pulled gastrointestinal wall is then released and clip 80 resumes its austenitic circular configuration as shown in FIG. 1D.

The mechanism by which hypodermic needle 90 and/or push bar 93 is advanced from or retracted into collar 106 is any suitable mechanism as is known in the art. For example, this mechanism can include a pulley and cable mechanism, a fluid pressure and piston mechanism, or a gear driven (e.g., rack and pinion) mechanism. A pulley and cable system, however, is preferred as it is the most simple of these systems.

The present invention provides a reliable, definitive treatment for the problem of gastrointestinal bleeding. Moreover, the present invention provides hemostatic clips that are deployable via natural body orifices and without the manipulation of temperature. When deployed in accordance with the present invention, the clips provide sufficient strength to produce permanent hemostasis.

It will be obvious to those skilled in the art, having regard to this disclosure, that other variations on this invention beyond those specifically exemplified here may be made. Such variations are, however, to be considered as coming within the scope of this invention as limited solely by the following claims.

What is claimed is:

1. An arrangement for achieving hemostasis of ulcer beds comprising:

two pairs of gastrointestinal clips, the clips exhibiting pseudoelastic behavior at body temperature, wherein the clips comprise nitinol characterized by air $A_s$ temperatures less than body temperature and an $M_d$ temperature greater than body temperature, and wherein the clips have a substantially circular configuration when the nitinol is in a substantially austenitic state and whereby the gastrointestinal clips have sufficient strength to cause the hemostasis of an ulcer bed; and a delivery device capable of housing at least two pairs of gastrointestinal clips.

2. The arrangement of claim 1, wherein the delivery device is pre-loaded with the pairs of gastrointestinal clips.

3. The arrangement of claim 2, wherein each gastrointestinal clip is pre-oriented in the pre-loaded delivery device.

4. The arrangement of claim 1, wherein the delivery devise is a steerable endoscope.

5. The arrangement of claim 4, wherein the endoscope comprises a collar which houses the pairs of circular clips.

6. The arrangement of claim 5, wherein the pairs of clips are arranged in the collar such that each of a first pair of clips is parallel to each other and each of a second pair of clips is parallel to each other, said first pair of clips being orthogonal to said second pair of clips.

* * * * *